United States Patent [19]
Schmid

[11] Patent Number: 5,423,314
[45] Date of Patent: Jun. 13, 1995

[54] INTRODUCTION APPARATUS FOR A FETAL SCALP ELECTRODE

[75] Inventor: Alfons Schmid, Boeblingen, Germany

[73] Assignee: Hewlett Packard Company, Palo Alto, Calif.

[21] Appl. No.: 101,426

[22] Filed: Aug. 2, 1993

[30] Foreign Application Priority Data

Aug. 26, 1992 [DE] Germany ............... 42 28 351.5

[51] Int. Cl.⁶ .......................................... A61B 5/0448
[52] U.S. Cl. .................................................. 128/642
[58] Field of Search ................. 128/642; 607/127, 131

[56] References Cited

U.S. PATENT DOCUMENTS

| | | | |
|---|---|---|---|
| Re. 28,990 | 10/1976 | Hon et al. | 128/642 |
| 3,750,650 | 8/1973 | Ruttgers | 128/642 |
| 3,804,080 | 4/1974 | Ruttgers et al. | 128/642 |
| 4,281,659 | 8/1981 | Farrar et al. | 128/642 |
| 4,301,806 | 11/1981 | Helfer | 128/642 |
| 4,321,931 | 3/1982 | Hon | 128/642 |
| 4,836,208 | 6/1989 | Ulbrich | 128/642 |
| 4,934,371 | 6/1990 | Malis et al. | 128/642 |
| 5,012,811 | 5/1991 | Malis et al. | 128/642 |

FOREIGN PATENT DOCUMENTS

| | | | |
|---|---|---|---|
| 2061593 | 5/1972 | Germany . | |
| 2738479 | 3/1979 | Germany . | |
| 148184 | 5/1981 | Germany | 128/642 |
| 786985 | 12/1980 | U.S.S.R. | 128/642 |

*Primary Examiner*—Lee S. Cohen

[57] ABSTRACT

An introduction apparatus for a fetal scalp electrode comprises an electrode head that is rotatably fixed but disengageably connected to an inner tube. During introduction, both are surrounded by an outer tube. According to the invention, there is also a disengageable driving connection between the electrode head and the outer tube. This driving connection is configured in preferred embodiments of the invention as a bayonet connection, or as a spring-loaded stop apparatus. Further embodiments provide for a shearable or threaded-like connection.

17 Claims, 6 Drawing Sheets

INTRODUCTION APPARATUS FOR A FETAL SCALP ELECTRODE

FIELD OF THE INVENTION

The present invention relates to an introduction apparatus for a fetal scalp electrode, including an electrode head that, at least during introduction of the scalp electrode, is rotatably fixed, but disengageably connected to an inner member, preferably an inner tube, and an outer tube into which the electrode head and the inner member are at least partially inserted during introduction of the scalp electrode.

BACKGROUND OF THE INVENTION

Scalp electrodes of the type under discussion herein are used to record the heart rate of the unborn fetus before and during birth. The electrode is introduced vaginally and fastened to the scalp of the fetus, usually by screwing in a spiral wire. It is understood that this monitoring method—also called "direct ECG"—can only be used after rupture of the membranes. Prior to that, other monitoring methods such as the Doppler ultrasound method have to be used.

The physiological signal derived from the scalp of the fetus is usually fed to an analysis unit that extracts the individual heartbeats (for example the R waves of the ECG) and uses them to determine the heart rate from beat to beat (for example as the reciprocal of the time interval between two heartbeats). The heart rate obtained in this manner is referred to as a "beat-to-beat" heart rate. Its time profile, shape, and reproduced frequency components provide a series of important diagnostic data concerning the fetal condition. This applies particularly if, concurrently with the heart rate, the mother's labor activity is also recorded. The correlation between the two measured variables also provides significant diagnostic information. For example, oxygen deficiency in the fetus due to a loop in the umbilical cord can be detected promptly, and suitable countermeasures (such as Caesarean section) can be taken. Devices or monitors that record fetal beat-to-beat heart rate and maternal labor activity are also known as cardiotocographs or fetal monitors.

Of the various possibilities for deriving the baby's heart rate, direct ECG derived with a fetal scalp electrode supplies by far the best signal, since the transducer is in galvanic contact with the fetal body. When the mother is bearing down this is in fact, according to the present state of the art, the only way to obtain a reliable heart rate indication. Nevertheless, unlike the other methods such as Doppler ultrasound, heart sound measurement, etc., this is an invasive measurement method with all the associated disadvantages. An additional complicating factor is that because of the vaginal introduction, the scalp electrode is difficult to apply.

In the past, various aids had already been developed to facilitate application of the scalp electrode. The typical introduction aid comprises an outer tube in which the electrode head (with the spiral wire or some other fastening means at its proximal end) and a cylindrical inner member, preferably an inner tube, are arranged. The electrode head and the inner tube are connected rotatably fixed (i.e., nonrotatably with respect to each other) but disengageably, for example by means of a bracket extending back from the electrode head into a recess of the inner tube, or a suitable square piece. The outer tube holds these two elements together during the introduction and application process, and protects both the mother and the baby from inadvertent injury due to the spiral wire, since the outer tube projects beyond the wire during the introduction process.

To apply the electrode, the doctor first introduces the outer tube into the birth canal until it touches the fetal scalp. Holding the outer tube with one hand, he then slides the inner tube forward with the other hand until the spiral wire attached to the electrode head touches the baby's head. Then the inner tube is rotated so that the spiral electrode perforates the fetal scalp and penetrates into it. The inner tube can now be withdrawn; this is possible because the electrode head and inner tube are not fastened to one another axially. Then the outer tube is also withdrawn.

In conventional designs the connecting wire of the electrode head is guided through the inner tube; after the two tubes are pulled out, the connecting cable remains in the birth canal and, after application, is connected to a suitable monitoring unit, for example a fetal monitor. Of course it is also possible to provide, instead of a connecting wire, for telemetric transmission or the like, although so far no scalp electrodes based on this principle are available on the market.

Fetal scalp electrodes of the aforesaid type are known in the art and have already been mentioned frequently in the patent literature, for example in U.S. Pat. No. 28,990 or U.S. Pat. No. 4,301,806.

One significant problem with the introduction mechanism for fetal scalp electrodes just described is its complex and unsafe handling. For example, it may happen that the inner tube is not kept in constant engagement with the electrode head. In this case it is no longer possible to transfer torque from the inner tube to the electrode head, such that the electrode cannot be applied. If this happens, the introduction aid must be withdrawn. Although it would theoretically be possible to bring the inner tube and the electrode head back into engagement, this would require grasping the electrode head, meaning that its sterility cannot be guaranteed. If disposable parts are used, they must therefore be discarded. Resterilization is required even in the case of reusable parts.

A feature already known in the art that eliminates the aforementioned problem consists in guiding the electrode cable through the inner tube and clamping it at the distal end of the inner tube. If tension is exerted on the connecting cable, it keeps the electrode head in contact with the inner tube so that the latter cannot unintentionally become detached. According to another solution, also known, a clamp can be placed on the electrode cable, said clamp being applied to the distal end of the inner tube.

Both proposals, however, have the critical disadvantage that the doctor or midwife applying the electrode must not under any circumstances forget to disengage the clamping of the electrode cable after the electrode is applied. If this is forgotten, the electrode is withdrawn together with the inner tube, so that the spiral wire is torn out of the skin of the fetal head. The known devices therefore entail a considerable risk of injury to the baby. There also exists a further handling problem that is not solved by clamping the electrode cable, and that can be described as follows:

During introduction it is necessary to maintain the relative position of the inner and outer tubes. For example, if the inner tube is pushed forward a bit too far, the spiral wire projects out of the introduction aid and may injure the mother or the baby. On the other hand, if the outer tube is inadvertently pushed too far forward, it may happen that the electrode head is driven along with it and disengages, in the manner already mentioned, from the inner tube.

Upon introduction of the electrode, the doctor must therefore use one hand to grasp both the outer tube, and the inner tube projecting from it, at their distal ends, thus establishing the relative position of the two tubes. With the same hand he must also advance the introduction aid; the second hand is needed to guide the outer tube. It is evident that this type of handling is extremely inconvenient.

One proposal, known from the prior art, for solving this second problem consists in mutual locking of the inner and outer tubes, for example by means of a snap lock. However, with these introduction aids (also known) the connector cable for the electrode must be manually retained in order to prevent the electrode head from disengaging from the inner tube.

It would be possible to combine the two features discussed above—clamping the electrode cable and mutually snap-locking the inner and outer tube although this attempt has not yet been made in practice. It is evident, however, that even this combination would not completely solve the underlying problems, since in order to prevent injury to the fetus one must under no circumstances forget to disengage the electrode cable clamp. This problem is fundamentally bound up with the use of a clamping mechanism, and cannot be eliminated even by combining the two features described above. In addition, the mechanical features required to snap-lock the two tubes and clamp the electrode cable are very complex, and increase the manufacturing costs of the electrode.

SUMMARY OF THE INVENTION

The underlying purpose of the present invention is therefore to provide an introduction aid of the aforesaid type that eliminates the said disadvantages. In particular, the intent is to improve handling and reduce the danger of injury.

In an introduction apparatus of the kind discussed at the outset, this object is achieved by a disengageable driving connection between the electrode head and the outer tube. As already mentioned, a rotatably fixed, disengageable connection between the inner tube and the electrode head has been part of the prior art for some time. The invention, however, proposes as an additional feature also to provide a driving connection between the electrode head and the outer tube. Thus the electrode is retained at the outer tube during introduction, and released, by means of an unlocking or similar mechanism, for application only after the introduction process.

The invention makes a snap-lock mechanism between the inner and outer tubes (which also suffers from other disadvantages) superfluous. Moreover, locking (clamping) of the cable can also be omitted; the cable no longer needs to be held under tension in order to hold the electrode head in position so that it cannot slide forward and cause injury. According to the invention, this task is performed by the disengageable driving connection between the electrode head and the outer tube.

This embodiment of the introduction aid is technically simple to manufacture, and its advantages are superior to all known solutions and even to a combination of these known solutions. In particular, there is no longer any danger at all that the electrode head will slide forward during the introduction process and that the spiral wire, now projecting out of the outer tube, will cause injury. The electrode cable is not pre-tensioned by a clamping apparatus and thereby not exposed to stress; in addition, since the electrode cable no longer needs to be fastened at its distal end, the danger that the spiral wire will be pulled out of the fetal scalp is eliminated.

Lastly, the handling of the introduction aid is also considerably simplified. For example, the doctor can guide the outer tube with the left hand and with the right hand exert pressure on the inner tube in order to produce the required forward motion. This eliminates the need to monitor the relative position of the inner and outer tubes. It is even possible to transmit rotary motions, specifically from the inner tube to the electrode head and from there to the outer tube, so there is no need to rotate the two tubes synchronously with one another.

In some (but not all) embodiments of the invention, the rotatably fixed connection between the inner tube and the electrode head is configured such that the inner tube can be withdrawn, thus abolishing the positive engagement between the two parts. But even in this case, the connection can easily be reestablished by pushing the inner tube forward again, and rotating it until its front end again locks together with the electrode head. This was not possible with embodiments according to the prior art, since reassembly required grasping the electrode head which thereby became unsterile, such that the introduction aid was then no longer clinically usable. With the introduction aid according to the invention, however, the electrode head is held in its position in the outer tube, so that it does not need to be grasped and sterility can therefore be guaranteed.

It is advantageous if the disengageable driving connection between the electrode head and the outer tube is effective, prior to disengagement, in the axial direction of the outer tube, so that an advancing force exerted on the inner tube is also transferred to the outer tube. This function can be provided, for example, by a bayonet connection or a stop apparatus, both of which have yet to be discussed. It is also advantageous, however, if the driving connection is rotatably fixed, at least when a torque below a certain maximum amount is applied, so that torsional forces between the inner and outer tube can also be transferred. When a torque in excess of the maximum amount is applied, however, the driving connection should disengage to allow the scalp electrode to be "screwed into" the fetal scalp. In other words, the driving connection can be disengaged by rotating the electrode head relative to the outer tube, specifically by applying a certain torque.

In a further preferred embodiment, the driving connection has a snap-locked position. This ensures that the driving connection does not disengage when only a low level of torque is applied. A low level of torque of this kind may be necessary to apply the introduction aid properly, or may also be exerted unintentionally.

Application of the scalp electrode is considerably simplified if the distal end (away from the head) of the inner member is attached to a turning knob. With this, rotary or torsional forces can be generated precisely and easily, for example a first torque that disengages the driving connection between electrode head and the outer tube, and a second torque that is needed to screw the spiral electrode into the fetal scalp.

In the case of a scalp electrode with a connecting cable, the latter is preferably fastened to the electrode head and guided through the inner member. The most favorable configuration therefor is a hollow inner tube through which the connecting cable is guided. The related advantage is that the connecting cable cannot, for example, become jammed between the inner and outer tube.

In a first advantageous embodiment of the invention, the disengageable driving connection between the electrode head and the outer tube is configured as a bayonet connection. The bayonet connection can transmit axial forces and—to a certain degree—torques as well. Advantageously, the bayonet connection can be configured so that the electrode head has at least one—preferably two—pins projecting radially outward, which run(s) in a gated guide of the outer tube. A bayonet connection of this type is particularly easy to manufacture. But it is also possible, of course, to reverse the operating principle and attach the pins to the inside of the outer tube, with the gated guide on the outside of the electrode head.

A bayonet connection of this kind is especially stable if the outer tube is internally reinforced at least in the region of the electrode head, and if the gated guide is located within this reinforcement. The reinforcement can consist in the fact that material with a greater wall thickness is used at the proximal end of the outer tube; or a second tube, pressed or adhesively bonded into the proximal end of the outer tube, can be used.

Advantageously, the gated guide (link guide) of the bayonet connection has a snap-lock recess. This reliably guarantees that the pins of the electrode head snap out only when a certain torque is applied, such that the electrode head can be slid toward the fetal head by means of pressure exerted on the inner tube. Further rotation causes the spiral wire to be "screwed" into the baby's scalp. The two insertion tubes can then be withdrawn.

In another, particularly preferred embodiment, the disengageable driving connection consists of a stop means acting between the outer tube and the electrode head, as well as spring means acting in the axial direction on the electrode head. The stop means prevents the electrode head from sliding forward out of the outer tube. Advantageously, the stop means is designed so that the electrode head can slide forward in a certain angular position (rotational angle with respect to the outer tube), for example by using at least one (preferably two) snap lugs and at least one pin engaging in the snap-lock recess of the snap lug. For reasons of manufacturing engineering, it is preferable in this context to arrange the snap lug on the inner wall of the outer tube and the pins on the electrode head, although in theory the reverse arrangement would be possible as well.

The spring means pushes the electrode head towards the proximal end of the outer tube and thus ensures that it is in contact with the stop means; at the same time this prevents the electrode head from moving backward. The spring means thus has two functions, i.e. that of spring-loaded locking and that of a stop for the electrode.

A third function that is important in clinical practice involves final guidance of the electrode, i.e. of the electrode head and the spiral wire. Since the head of the fetus is convex, in known spiral electrodes the electrode is often not given sufficient final guidance, i.e. is not held in constant contact with the scalp. The spiral wire then cannot be precisely screwed in, meaning that the electrode is then only partly screwed in and can become detached. This disadvantage is also overcome by the spring means according to the invention, since the spring bridges the final guidance region—i.e. presses the electrode head by spring pressure against the scalp—thus improving application of the electrode.

In terms of manufacturing engineering, it is especially favorable if the outer tube consists of a base member and an attachment member, the stop means being provided on the attachment member.

In one favorable embodiment, the spring means is a compression spring braced against an internal projection of the outer tube or of its attachment member, respectively. The compression spring may comprise a plurality of radial elements that are connected by lateral webs running in the axial direction. The advantage of this configuration is that the compression spring can be manufactured, in an economical manner, from plastic material. This is especially recommended for introduction aids that are used only once and then discarded.

Radial driving of the electrode head by the inner tube can be guaranteed, for example, by a receptacle, preferably an indentation, on the end of the compression spring facing the electrode head. A rotation-prevention element that is applied onto the distal end of the electrode head engages in this receptacle.

The inner member or the inner tube may be in contact with the distal end of the compression spring. In a particularly favorable embodiment, the inner member and the compression spring are attached to each other, for example by press-fitting. The not inconsiderable advantage of this is that the inner member cannot be inadvertently withdrawn, since the compression spring for its part is in contact with an internal projection of the outer tube. The problem whereby the rotatably fixed but disengageable connection between the inner member and the electrode head may be disengaged during the introduction process therefore no longer exists with this embodiment.

In a further embodiment according to the invention, the electrode head is connected to the outer tube by means of a shearable connection, the connection preferably being shearable by means of rotation. The shearable connection can consist of a web, for example—in the case of disposable introduction aids—a plastic web. A connection of this type guarantees reliable transmission of axial forces and torques between the electrode head and the outer tube, and therefore also between the inner and outer tubes. Alternatively, the disengageable driving connection can also consist of a threaded-like connection, for example a standard or trapezoidal thread or an inclined plane. In order to improve handling, this threaded-like connection can furthermore be provided with a snap catch, for example a snap lug and a pin that snaps into it.

The invention also refers to a method for applying a fetal scalp electrode of the aforesaid type, application comprising the following steps:

Disengaging a disengageable driving connection between the electrode head and the outer tube; and
applying a wire, preferably a spiral wire, arranged at the proximal end of the electrode head onto the scalp of the fetus by rotating the inner member and thus the electrode head.

Rotation can be performed by rotation of the inner member relative to the outer tube, preferably by means of a turning knob.

BRIEF DESCRIPTION OF THE DRAWINGS

Further features and advantages of the invention are evident from the dependent claims and from the description referring to the drawings, in which preferred embodiments of the invention are depicted. In the drawings:

FIG. 1 shows an introduction aid for a fetal scalp electrode, labeled as a whole as 1. The electrode itself consists of an electrode head 2 that carries a spiral wire 3. This spiral wire is intended to perforate and penetrate into the fetal scalp in order to derive the heart rate.

Figure 1:
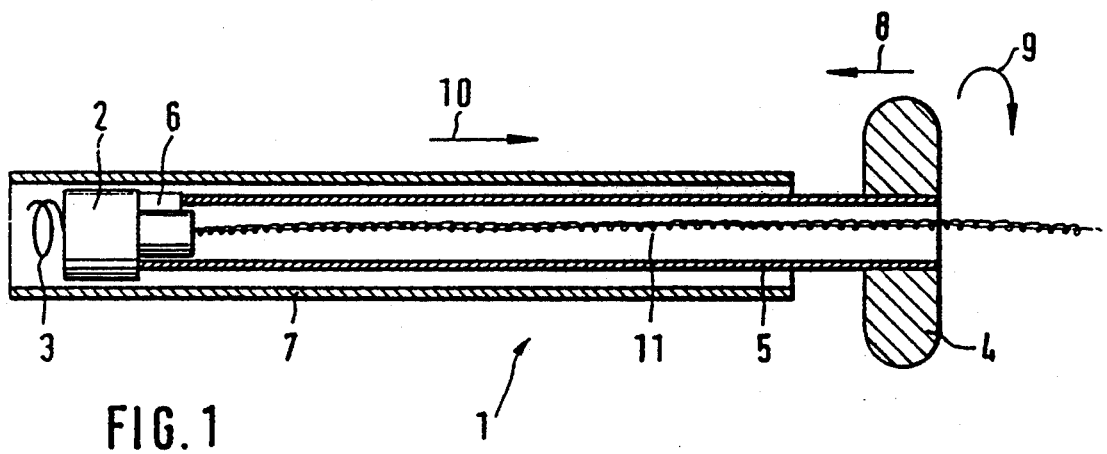
FIG. 1 shows a longitudinal section through an introduction aid known from the prior art.

An inner tube 5 permanently attached to a turning knob 4 is connected rotatably fixed but disengageably to the electrode head 2. A web 6 or other rotation-prevention element, engaging in corresponding slots of the inner tube 5, can be used for this purpose. In most practical instances two diametrically opposite webs are used, but only one web 6 is shown in FIG. 1 for illustrative purposes.

During the introduction process, the combination of electrode head 2 and inner tube 5 is surrounded by an outer tube 7, which keeps the other components together and prevents the spiral wire 3 from injuring the mother or the baby.

For the purpose of application, the introduction aid is first introduced vaginally until the left (in FIG. 1) end surface of the outer tube 7 touches the fetal scalp. Then the inner tube is slid into the outer tube 7 in the direction of arrow 8, causing the spiral wire 3 to touch the baby's scalp. The spiral wire 3 is screwed into the fetal scalp by subsequently rotating the turning knob 4 in the direction-of arrow 9. Then the outer tube 7 and the inner tube 5 are withdrawn in the direction of arrow 10, leaving the electrode connector wire 11 behind. Once the electrode cable has been connected to a suitable monitoring unit, the fetal heart rate can be recorded.

FIG. 1 shows an introduction aid known from the prior art. It is immediately evident that handling is cumbersome, and entails a risk of injury. For example, inadvertent withdrawal of the inner tube 5 can disengage the engagement between inner tube 5 and electrode head 2. This connection cannot be reestablished, since that would require grasping the electrode head 2 and the outside of the outer tube 7. This would, however, destroy the sterility of the arrangement.

If the inner tube 5 is inadvertently pushed too far into the outer tube 7 during the introduction process, the spiral wire 3 may project out of the outer tube 7 and thereby injure the mother or baby. The doctor has therefore to ensure, during introduction, that the relative positions of the inner tube 5 and outer tube 7 remain unchanged, for example by holding onto the turning knob 5 and the outer tube 7 with one hand. This is, however, very uncomfortable and error-prone.

Moreover, the electrode head 2 itself must also be prevented from sliding too far forward (to the left in the depiction of FIG. 1 ). The electrode cable 11 must therefore also be fastened in some manner, for example by also being held onto.

Figure 2:
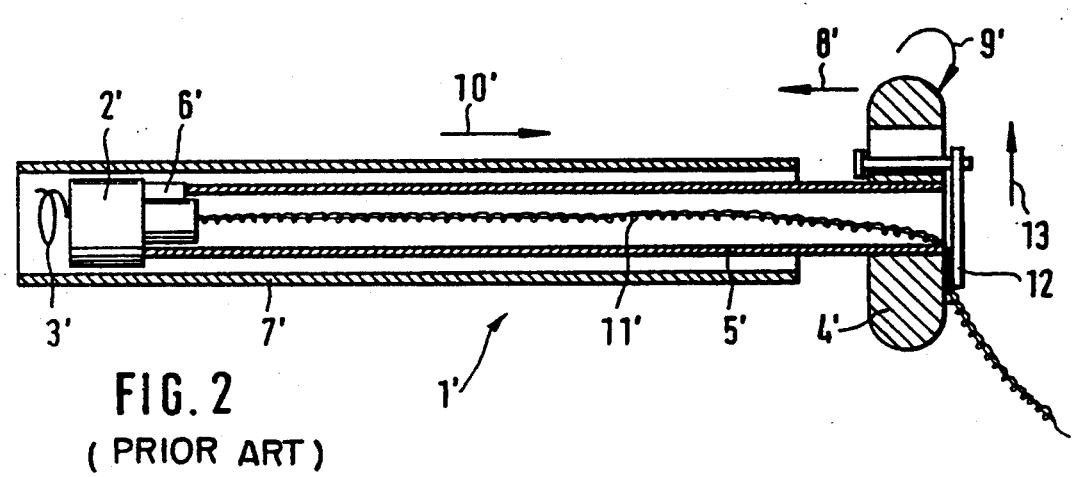
FIG. 2 shows an improved, also previously known introduction aid, in longitudinal section.

A first attempt of a solution eliminating these problems, also known from the prior art, is shown in FIG. 2. To the extent that the components shown there are identical to those of FIG. 1, the same reference numbers have been used, but with an apostrophe added. In this embodiment a clamp (clamping lock 12) is provided, which retains the electrode cable on the turning knob 4'. This prevents the electrode head 2' from moving too far away from the inner tube 5', such that neither the connection between electrode head 2' and inner tube 5' can be disengaged, nor the spiral wire 3' can project out of the outer tube. An additional step, labeled 13 in FIG. 2, is also necessary, namely disengagement of the clamping lock.

One considerable disadvantage of the embodiment according to FIG. 2 is that after screwing in the scalp electrode, one must not under any circumstances forget to disengage the clamping lock 12. Otherwise the electrode, together with the inner tube, will be withdrawn, tearing out the fetal scalp.

Figure 3:
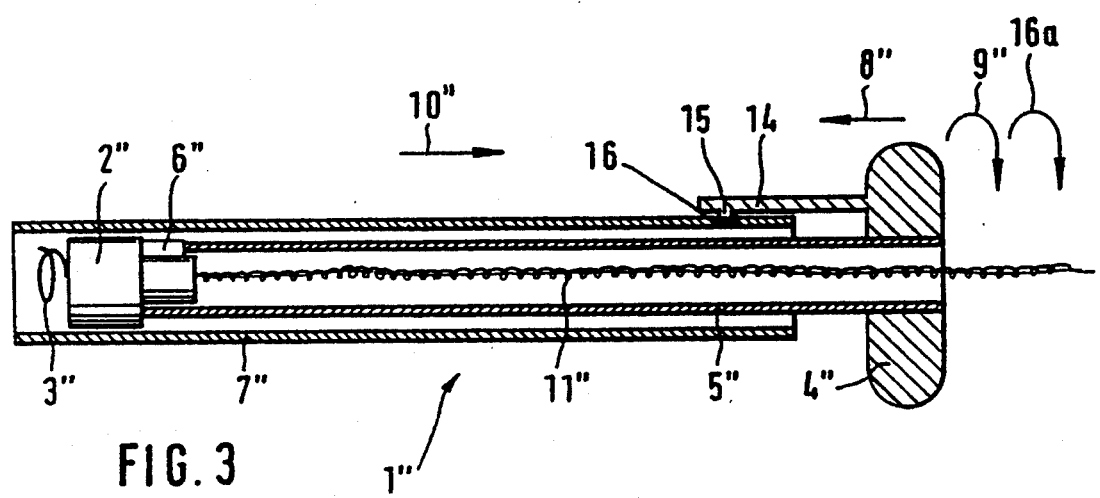
FIG. 3 shows the longitudinal section of a third introduction aid, also known from the prior art.

A third attempt of a solution, also known from the prior art, is shown in FIG. 3, marked with the same reference numbers as FIGS. 1 and 2, but with a double apostrophe added. In this case a snap lock is provided between the inner and outer tubes, namely by means of a snap-lock lever 14 formed onto the turning knob 4", the snap nose 15 of the snap-lock lever 14 engaging into an opening 16 in the outer tube 7". This fixes the relative positions of the inner and outer tubes. A further operating step is required during application, namely disengaging the snap lock as indicated by arrow 16a.

It is evident that the embodiment according to FIG. 3 does not solve the problem of the electrode cable, since the electrode head 2" can still slide from the inner tube 5". Even if the embodiments according to FIGS. 2 and 3 were combined, this would not eliminate the problem of possibly tearing out the electrode if one forgot to disengage the clamping of the electrode cable. Moreover, this solution would be very complex in design and would require a plurality of handling steps.

Figure 4:
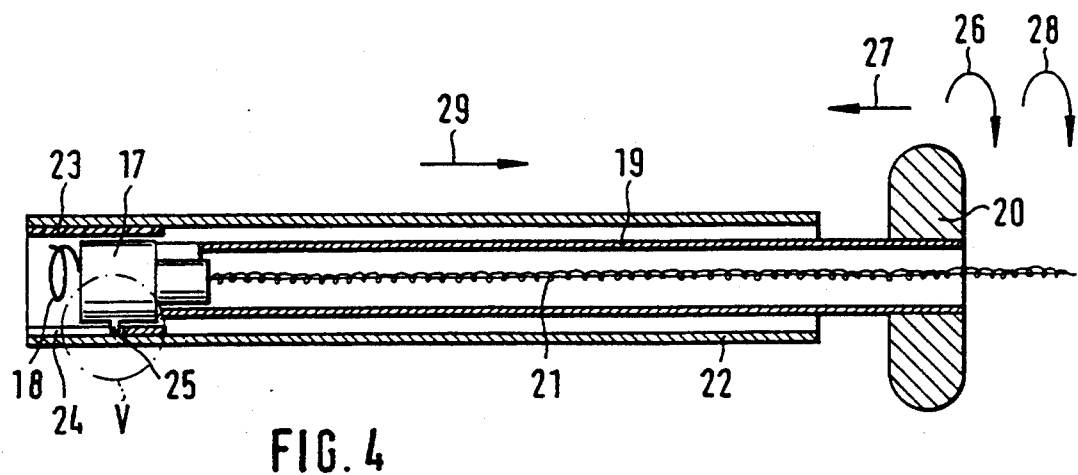
FIG. 4 shows the longitudinal section through an introduction aid according to a first embodiment of the invention.

FIG. 4 shows a longitudinal section through an introduction apparatus according to a first embodiment of the invention. The electrode head 17 (including the spiral wire 18) is in rotatably fixed engagement with the inner tube 19, as was also already the case with the embodiments according to the prior art. The inner tube 19 is attached to a turning knob 20; the connector cable 21 for the spiral electrode runs through the interior of the inner tube 19.

The rotatably fixed connection between electrode 17 and inner tube 19 is configured as in the known introduction aids.

The outer tube 22 includes in its end region (to the left in FIG. 4) a reinforcement 23. This reinforcement can, for example, consist of a plastic bushing that fits into the outer tube 22. The reinforcement 23 is furthermore provided with a gated guide 24 into which a pin 25, projecting from the electrode head 17, engages. For illustrative purposes, FIG. 4 shows only one pin and one gated guide, but it is understood that in practice, preferably two diametrically opposite pins and gated guides, or even more, are used.

Figure 5:
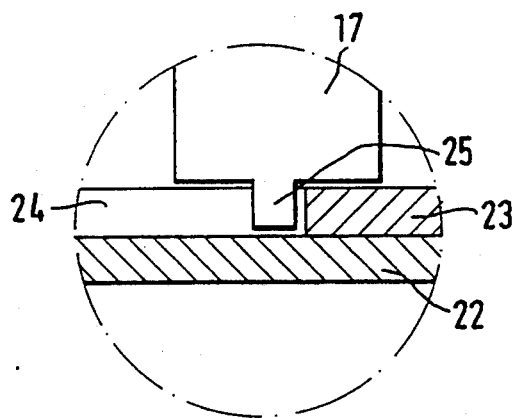
FIG. 5 shows detail V according to FIG. 4, in an enlarged scale.

The detailed drawing according to FIG. 5 shows the pin 25 and gated guide 24 in an enlarged depiction.

Figure 6:
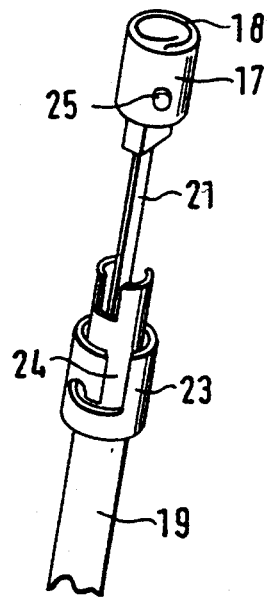
FIG. 6 shows an exploded view of certain parts of the new introduction aid shown in FIG. 4.

The detailed configuration of the gated guide is especially evident from FIG. 6, which shows a partial perspective view. In this drawing, the outer tube 22 has been omitted, and only the reinforcement 23, equipped with the gated guide, has been drawn. It is evident from this depiction how the pin 25 moves in the gated guide 24. As long as the inner tube (and thus the electrode head) is not rotated, the bayonet connection is locked in place, so that axial forces and—to a certain extent—peripheral forces as well can be transmitted. During application, the procedure is as shown by the arrows of FIG. 4. First the introduction mechanism is introduced until the end surface (to the left in the Figure) of the outer tube 22 contacts the fetal scalp. Then the turning knob 20 is rotated in the direction of the arrow 26, which unlocks the bayonet connection. The inner tube 19 and therefore the electrode head 17 can now be pushed forward in the direction of arrow 27 using the turning knob 20, until the spiral wire 18 is in contact with the fetal scalp. The electrode is screwed in in the direction of arrow 28. Then the introduction aid can be withdrawn in the direction of arrow 29.

Figure 7:
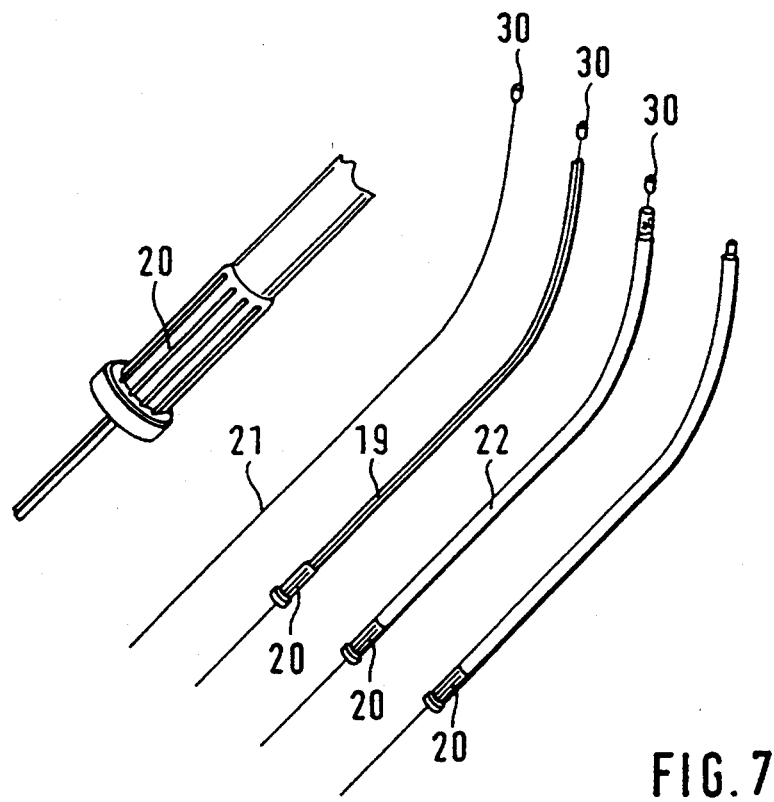
FIG. 7 shows the individual parts of the introduction aid according to the first embodiment of the invention.

FIG. 7 shows the various elements of the first embodiment of the invention, specifically the cable 21 with the spiral electrode 30 (consisting of electrode head and spiral wire) fastened to it, as well as the same arrangement, but including the inner tube 19 and turning knob 20. The assembled position including the outer tube 22 is also evident; lastly, the assembled state is shown at bottom right, although the spiral electrode has not yet been withdrawn completely into the outer tube. Also shown at top left is an enlarged perspective depiction of the turning knob 20.

Figure 8:
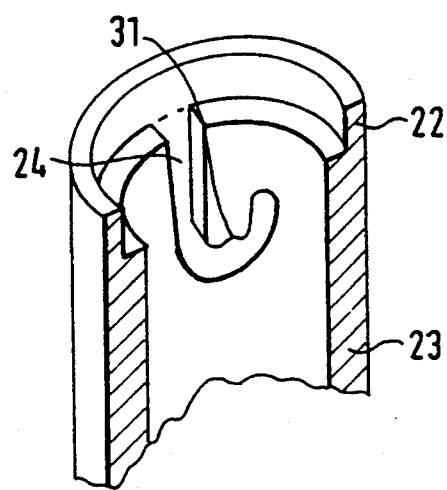
FIG. 8 depicts a detail of the first embodiment in a perspective and partly cut-away view.

The partly cut-away perspective drawing according to FIG. 8 shows the outer tube 22 including the reinforcement 23 into which the gated guide 24 (bayonet groove) is recessed. One detail not evident from the other drawings is a snap recess 31 that provides another snap-lock position for the pin 25 of the electrode head 17.

The embodiment just described is based on the fundamental idea of creating a disengageable driving connection between the electrode head and the outer tube. This basic idea can, of course, also be put into practice in ways not involving a bayonet apparatus. One example of this (second embodiment of the invention) is shown in FIGS. 9 to 15.

Figure 9:
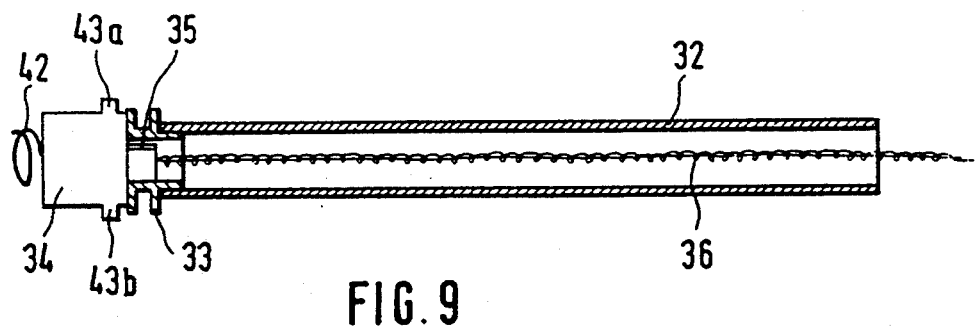
FIG. 9 shows a longitudinal section through an inner tube, a compression spring, and an electrode head according to a second embodiment of the invention.

FIG. 9 shows a longitudinal section through an inner tube 32 into one end of which a plastic compression spring 33 has been fitted. The compression spring 33 has a recess for a rotation-prevention element of the electrode 34, for example a web 35. The electrode connector cable 36 is guided through the interior of the inner tube 32.

Figure 10:
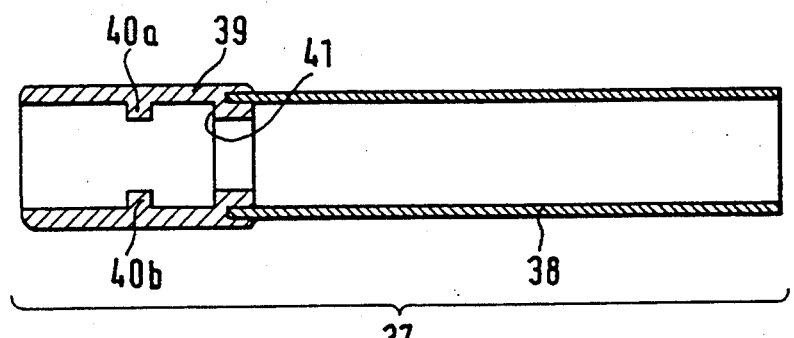
FIG. 10 shows the associated outer tube in longitudinal section.

FIG. 10 shows the associated outer tube 37. It consists of a base member 38 and an attachment member 39, connected to one another with a press fit. Snap lugs 40a, 40b, as well as a circumferential stop 41, are provided on the inner surface of the attachment member 39.

Figure 11:
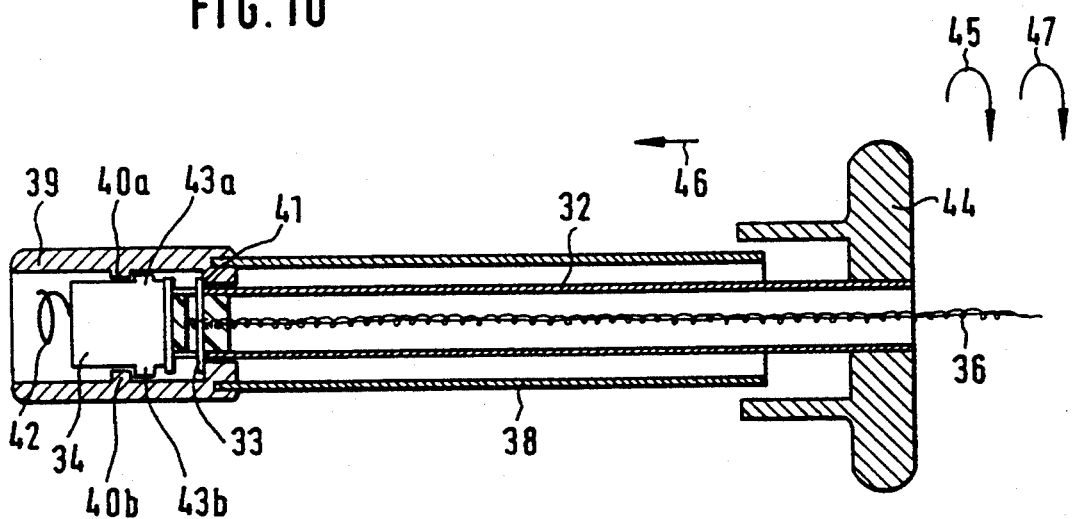
FIG. 11 shows the entire introduction aid according to the second embodiment of the invention, including the inner and outer tubes, the compression spring, and the electrode head.

FIG. 11 shows the introduction aid in its assembled state, in longitudinal section. The turning knob 44 is also evident here. The spiral wire of the electrode is labeled 42, as in FIG. 9.

The electrode head 34 has two snap lugs 43a and 43b (see also FIG. 9) which contact the snap lugs 40a and 40b of the attachment member 39 and snap into peace there. This occurs under the pressure of the compression spring 33, the end surface of which (to the right in FIG. 11) rests against the circumferential stop 41 of the attachment member 39. As a result, the electrode head 34 is held in its position defined by the contact with the snap lugs 40a and 40b.

This introduction aid is used as follows:

First it is introduced in the known manner. Then, by rotating the inner tube 32 clockwise (in the direction of arrow 45) with the turning knob 44, the pretensioned spring 33 is compressed and the snap-lock connection 40a/40b and 43a/43b is disengaged via the snap-lock or pressure point 40c.

The turning knob 44 can now be pushed in in the direction of arrow 46, which also pushes in the inner tube 32, the electrode head 34, and the spiral wire 42. As soon as the electrode head 34 is in contact with the fetal scalp, the turning knob 44 is rotated again (arrow 47), so that the spiral wire is screwed into the fetal scalp. Now the entire unit, with the exception of the spiral electrode itself, can be withdrawn. The grasping point in this case can be, for example, the turning knob 44. Since the spring 33 is in contact with the circumferential rim 41 of the attachment member 39, the outer tube—i.e. the base member 38 and the attachment member 39 connected thereto—is withdrawn. This is indicated by arrow 48.

Figure 12:
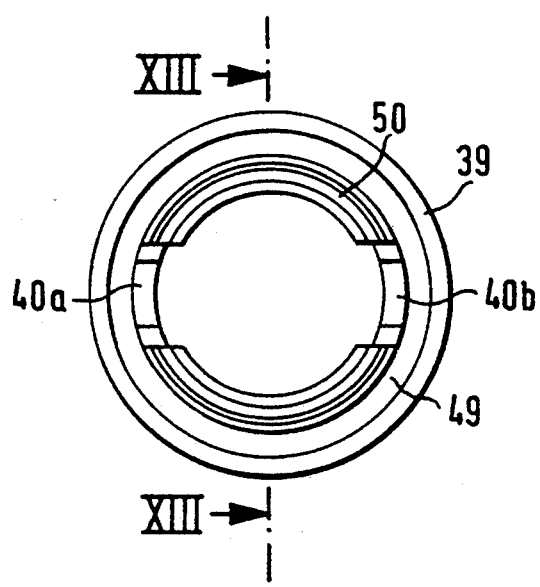
FIG. 12 shows the front view of an attachment member according to the second embodiment.

FIG. 12 shows the end view of the attachment member 39 as seen from the back, i.e. from the right in the depiction of FIG. 11. The base member 38 is pressed into the groove 49. The inner, circumferential flanks 50 each have recesses—to the right and left as depicted in FIG. 12—that are provided for reasons of manufacturing engineering. The two snap lugs 40a and 40b are visible through these recesses.

Figure 13:
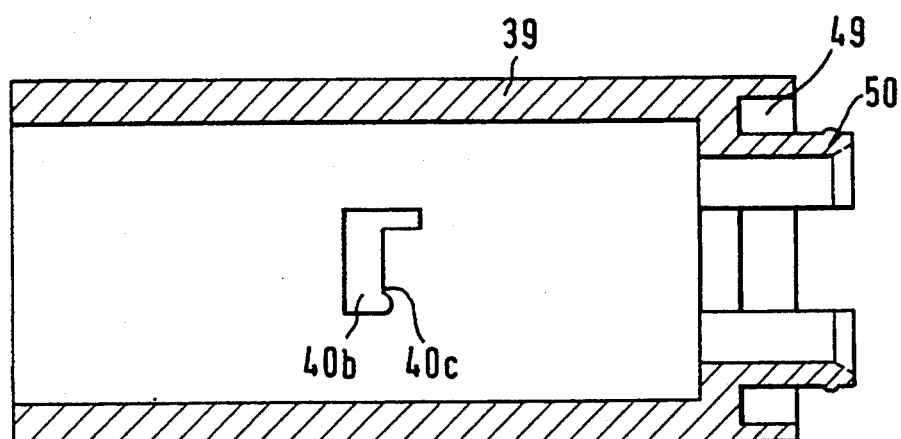
FIG. 13 depicts a section along reference line XIII—XIII of FIG. 12.

The outline of the snap lugs is even more evident from FIG. 13, which shows a longitudinal section along reference line XIII—XIII of FIG. 12.

Figure 14:
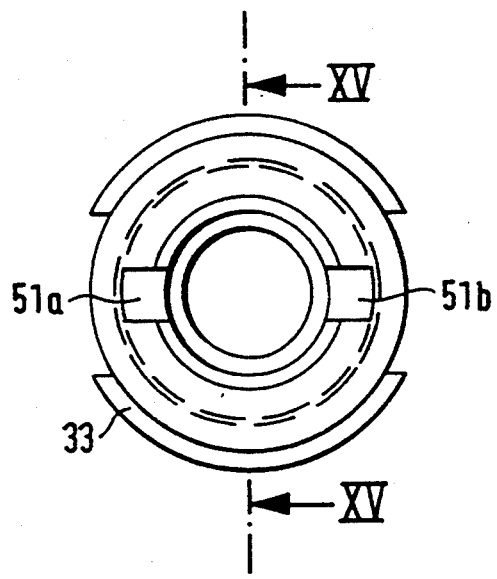
FIG. 14 shows the front view of the compression spring used in the second embodiment of the invention.
Figure 15:
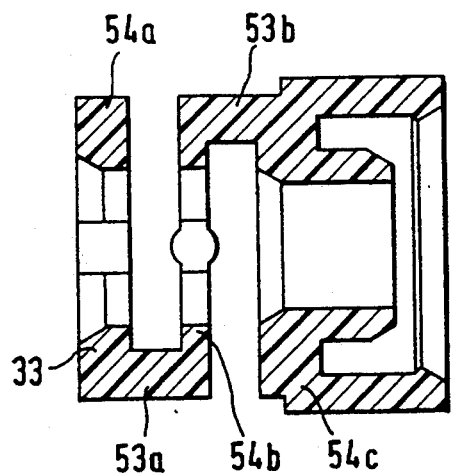
FIG. 15 shows a section along reference lines XV—XV of FIG. 14.

FIG. 14 shows the compression spring 33 as seen in a front view, i.e. from the left as depicted in FIG. 11. The cutouts 51a and 51b serve to receive a corresponding web (rotation-prevention element) arranged at the rear end of the electrode head 34, thus creating a rotatably fixed but disengageable connection. The cross section according to FIG. 15—along the reference line XV—XV of FIG. 14—shows webs 53a and 53b, which extend axially and connect corresponding radial elements 54a to 54c. These webs are flexible and provide the spring action.

The embodiment according to FIGS. 9 to 15 has the particular advantage that the rotatably fixed connection between the electrode head 34 and the compression spring 33 cannot be disengaged either by withdrawing the inner tube or by independent motion of the electrode head. This embodiment is therefore particularly safe and simple to operate.

Figure 16:
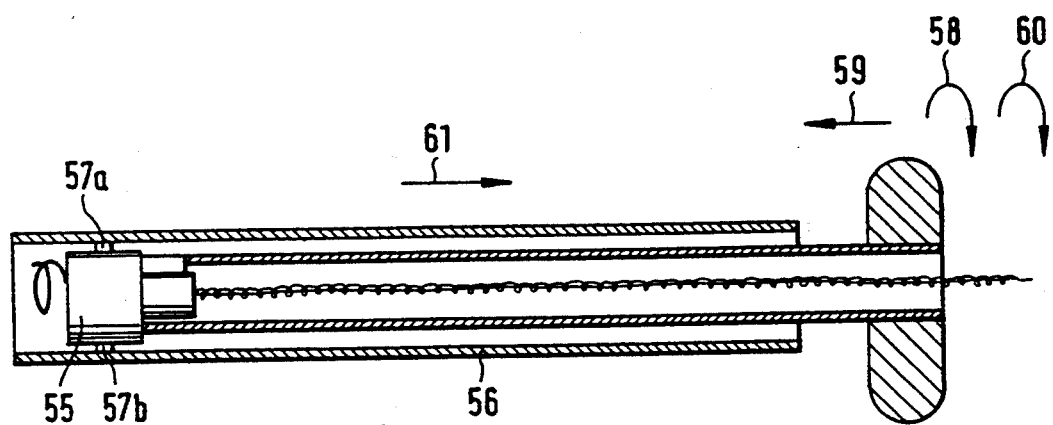
FIG. 16 shows a section through a third embodiment of the invention.

A longitudinal section through a further embodiment is shown in FIG. 16. Here the electrode head 55 is connected to the outer tube 56 by two shearable plastic webs 57a and 57b. The remaining components correspond to those of the foregoing Figures, and are not individually labeled in FIG. 16.

After introduction of the introduction aid shown in FIG. 16, the turning knob is first rotated in the direction of arrow 58, which shears off the webs 57a and 57b. The turning knob, together with the inner tube and the spiral electrode, can now be advanced in the direction of arrow 59. A further rotation—in the direction of arrow 60—causes the spiral electrode to be screwed into the fetal scalp; then the introduction aid can be withdrawn in the direction of arrow 61.

Figure 17:
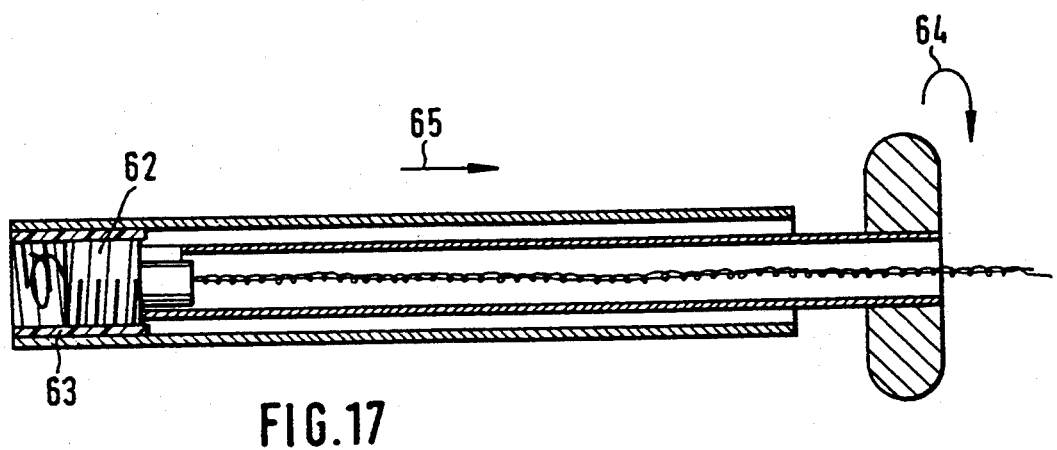
FIG. 17 depicts a section through a fourth embodiment.

In the embodiment according to FIG. 17, the electrode head 62 and a bushing 63 pressed into the outer tube are provided with corresponding threads. Rotation of the turning knob in the direction of arrow 64 therefore moves the spiral electrode towards the fetal scalp, and screws it in as rotation continues. The introduction aid can then be withdrawn in the direction of arrow 65. The thread used can, for example, be a standard or trapezoidal thread. An inclined plane is also possible. These threads or inclined planes may also additionally include snap-lock positions such that the .spiral electrode cannot be moved inadvertently.

I claim:

1. Introduction apparatus for a fetal scalp electrode including
    an elongated inner member,
    an electrode head including a scalp electrode that, at least during introduction of the scalp electrode, is rotatably fixed but disengageably connected to said inner member,
    an outer tube into which the electrode head and the inner member are at least partially inserted during introduction of the scalp electrode so as to position said scalp electrode near a proximal end of said outer tube, and
    a disengageable driving means for interconnecting the electrode head and the outer tube, said driving means having a snap-locked position which is released by a relative rotary pressure applied between said electrode head and said outer tube.

2. Introduction apparatus according to claim 1, wherein the driving means, prior to disengagement, comprises mating surfaces which interact to transfer an axial motion of said outer tube to said electrode head.

3. Introduction apparatus according to claim 1, wherein the driving means comprises mating surfaces that are rotatably fixed, upon application of a torque below a certain maximum amount.

4. Introduction apparatus according to claim 1, wherein the driving means includes mating surfaces that are disengageable by rotation of the electrode head by said inner member and relative to the outer tube.

5. Introduction apparatus according to claim 1, wherein a distal end of the inner member is attached to a turning knob.

6. Introduction apparatus according to claim 1, including an electrical connection cable, fastened to the electrode head and guided through said inner member.

7. Introduction apparatus according to claim 1, comprising:
    stop means positioned near a scalp-engaging end of said introduction apparatus between the outer tube and the electrode head for impeding axial movement of said electrode head along said outer tube, and
    spring means for axially biasing the electrode head to effect engagement of said stop means.

8. Introduction apparatus according to claim 7, wherein the stop means includes at least one snap lug and at least one pin engaging in a snap recess of the snap lug.

9. Introduction apparatus according to claim 8, wherein the snap lug is arranged on an inner wall of the outer tube, and the pin is arranged on the electrode head.

10. Introduction apparatus according to claim 7, wherein the outer tube comprises a base member and an attachment member, and wherein the stop means is provided at the attachment member.

11. Introduction apparatus according to claim 7, wherein the spring means includes a compression spring braced against an internal projection of the outer tube.

12. Introduction apparatus according to claim 11, wherein the compression spring includes a plurality of radial elements that are connected by lateral webs running in an axial direction.

13. Introduction apparatus according to claim 12, wherein the compression spring is made of plastic material.

14. Introduction apparatus according to claim 11, wherein the compression spring includes, at its end facing the electrode head; a receptacle for a rotation-prevention element that is applied onto a distal end of the electrode head.

15. Introduction apparatus according to claim 11, wherein the inner member is in contact with a distal end of the compression spring and is tightly connected thereto.

16. Method for applying a fetal scalp electrode wherein an electrode head is rotatably fixed, but disengageably connected to an inner member, and both the electrode head as well as the inner member are at least partially inserted into an outer tube during introduction of the scalp electrode,
    said method comprising the steps of:
        disengaging a disengageable snap-locked driving connection between the electrode head and the outer tube; and
        applying a spiral wire, arranged at a proximal end of the electrode head, onto the scalp of the fetus by rotation of the inner member and thus of the electrode head.

17. Method according to claim 16, further comprising the step of: rotating the inner member relative to the driving connection to cause disengagement of the disengageable driving connection.

* * * * *